(12) United States Patent
Chodorow

(10) Patent No.: US 8,196,587 B2
(45) Date of Patent: Jun. 12, 2012

(54) BRUXISM PROTECTIVE DEVICE

(75) Inventor: Ingram S. Chodorow, Rancho Sante Fe, CA (US)

(73) Assignee: Ranir LLC, Grand Rapids, MI (US)

( * ) Notice: Subject to any disclaimer, the term of this patent is extended or adjusted under 35 U.S.C. 154(b) by 559 days.

(21) Appl. No.: 12/316,922

(22) Filed: Dec. 16, 2008

(65) Prior Publication Data

US 2010/0147315 A1 Jun. 17, 2010

(51) Int. Cl.
A61C 5/14 (2006.01)
A61C 3/00 (2006.01)

(52) U.S. Cl. .......................... 128/861; 433/6

(58) Field of Classification Search ............... 128/846, 128/857, 859, 861–862; 433/2, 6, 9, 18–19
See application file for complete search history.

(56) References Cited

U.S. PATENT DOCUMENTS

| 4,867,147 A | 9/1989 | Davis |
| 4,976,618 A | 12/1990 | Anderson |
| 5,031,611 A | 7/1991 | Moles |
| 5,203,324 A | 4/1993 | Kinkade |
| 5,386,821 A | 2/1995 | Poterack |
| 5,682,904 A | 11/1997 | Stinnett |
| 5,692,523 A | 12/1997 | Croll et al. |
| 5,826,581 A | 10/1998 | Yoshida |
| 5,836,761 A | 11/1998 | Belvedere et al. |
| 5,873,365 A | 2/1999 | Brown |
| 5,879,155 A | 3/1999 | Kittelsen |
| 6,098,627 A | 8/2000 | Kellner et al. |
| 6,152,138 A | 11/2000 | Brown et al. |
| 6,200,133 B1 | 3/2001 | Kittelsen |
| 6,241,518 B1 | 6/2001 | Sullivan |
| 6,371,758 B1 | 4/2002 | Kittelsen |
| 6,494,209 B2 | 12/2002 | Kulick |
| 6,978,786 B2 | 12/2005 | Sabbagh |
| 2003/0111083 A1 | 6/2003 | Bancroft |
| 2004/0134499 A1* | 7/2004 | Sabbagh ...................... 128/859 |
| 2006/0084024 A1 | 4/2006 | Farrell |
| 2006/0096602 A1 | 5/2006 | Brown |
| 2007/0079835 A1 | 4/2007 | Croll |
| 2007/0148409 A1 | 6/2007 | Rios et al. |
| 2008/0138755 A1* | 6/2008 | Jansheski et al. ................ 433/6 |
| 2008/0138766 A1 | 6/2008 | Jansheski |
| 2009/0159089 A1* | 6/2009 | Jansheski ...................... 128/861 |
| 2009/0165805 A1* | 7/2009 | Syrop et al. ................... 128/861 |

FOREIGN PATENT DOCUMENTS

WO WO 2005/032438 A1 4/2005

OTHER PUBLICATIONS

Otuyemi, et al., "A comparison of crown size dimensions of the permanent teeth in a Nigerian and a British.population," European Journal of Orthodontics 18, 1996, p. 623-628.
International Search Report and Written Opinion, Mar. 31, 2010.

* cited by examiner

Primary Examiner — Patricia Bianco
Assistant Examiner — Tarla Patel
(74) Attorney, Agent, or Firm — Abelman, Frayne & Schwab

(57) ABSTRACT

A one-piece molded bruxism treatment device which in upright orientation has top and bottom parts, including: an elongated band having a generally U-shape defining a closed front end part and legs extending rearward and adapted to be positioned around the outer surfaces of a person's upper gums and teeth, and two generally planar resiliently deformable bite pads oriented generally horizontally, each extending from one of the feet of the band medially toward the other.

9 Claims, 6 Drawing Sheets

Figure 1:
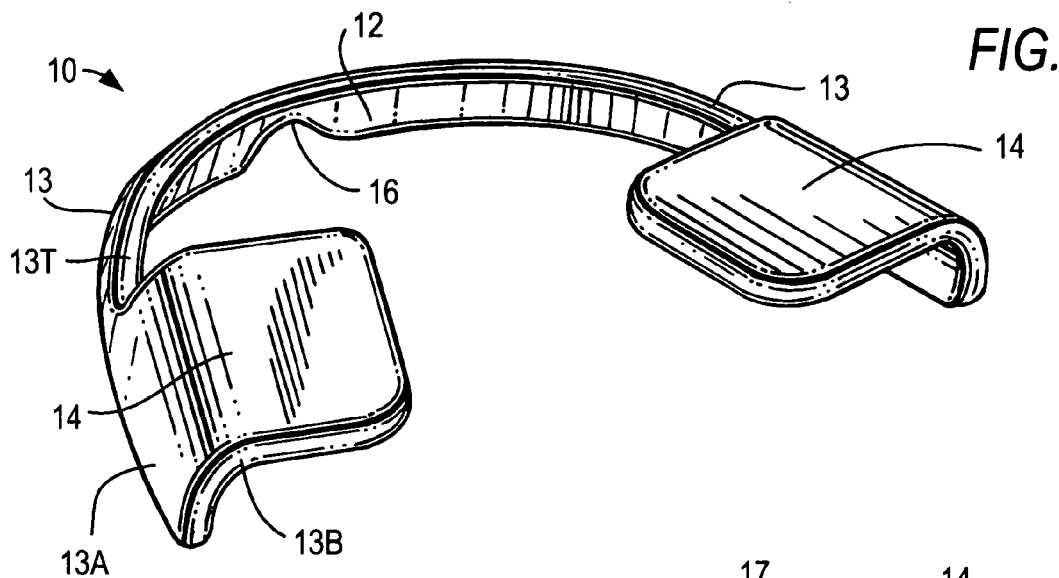

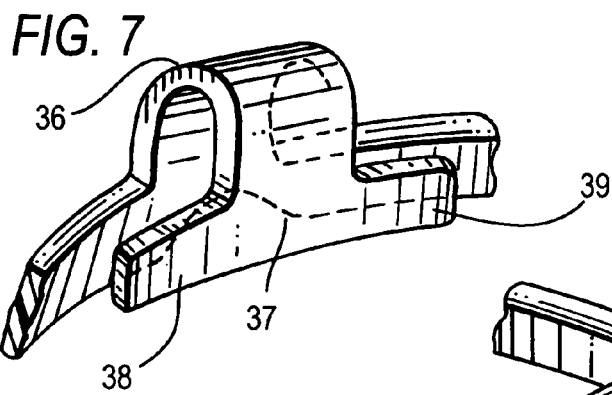
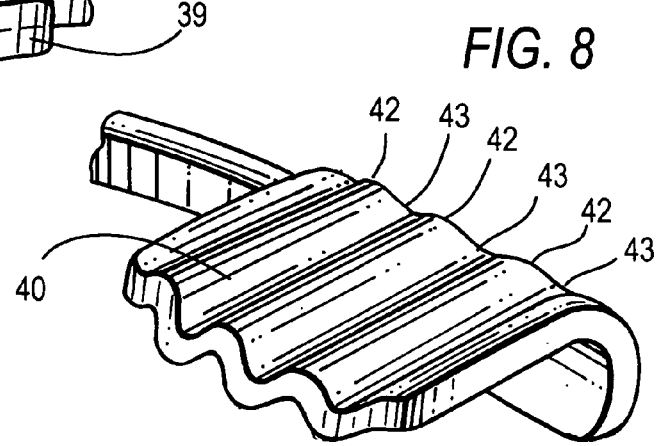
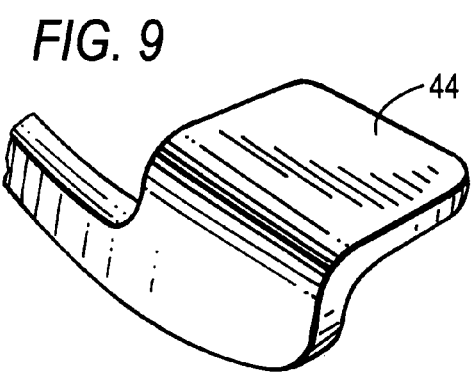
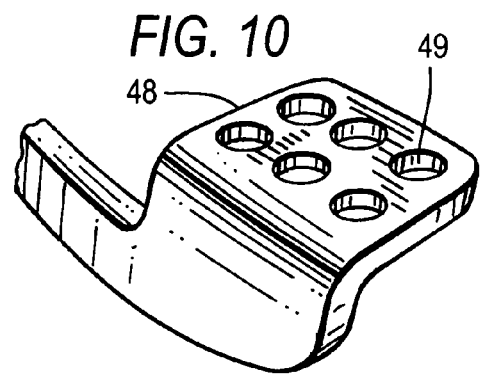
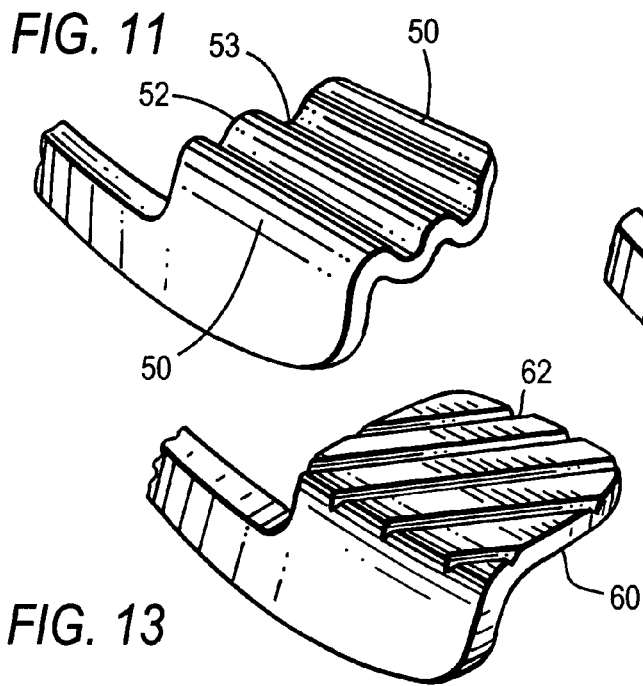
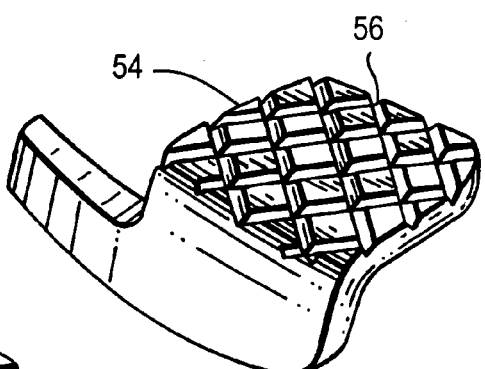

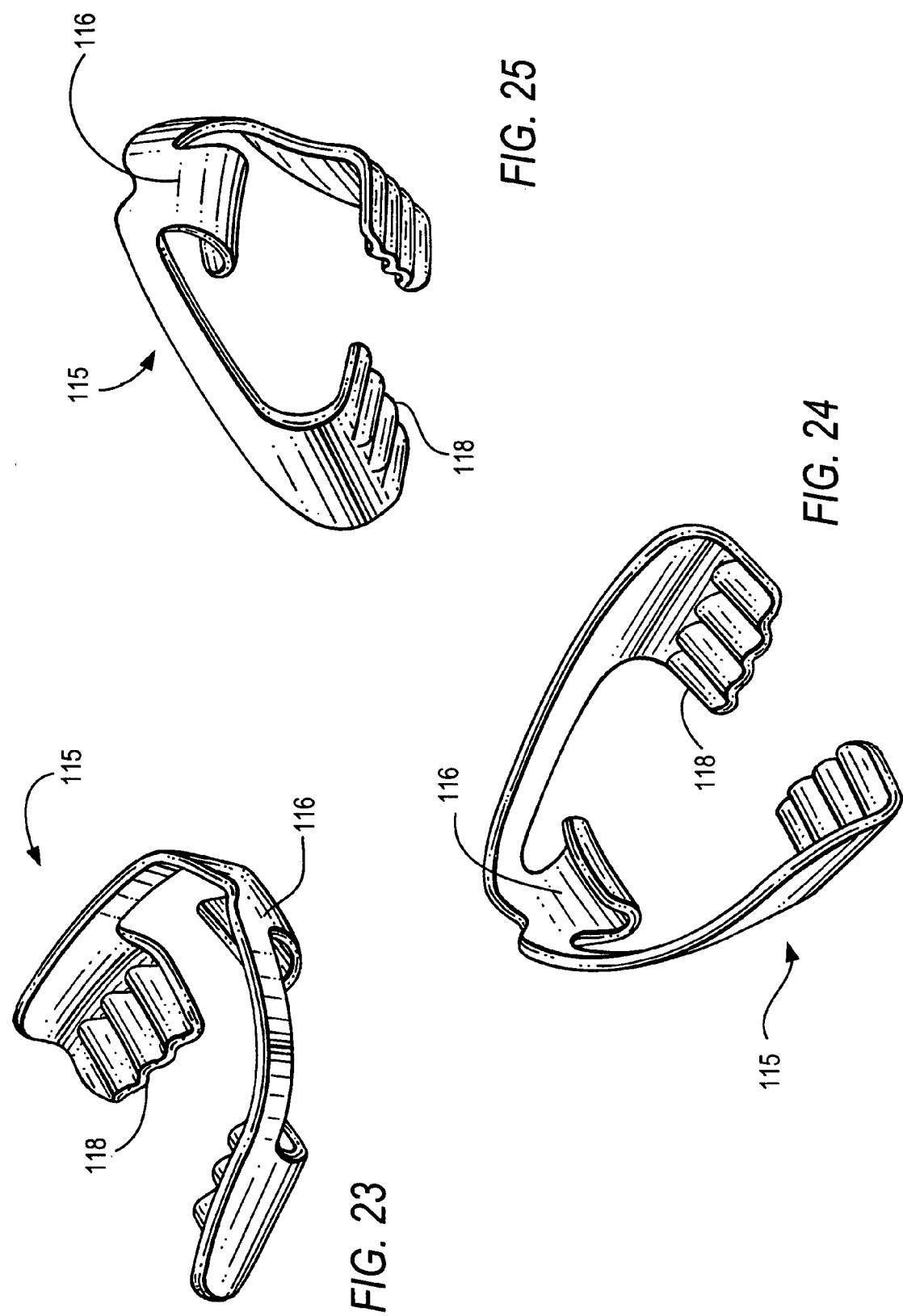

BRUXISM PROTECTIVE DEVICE

I. FIELD OF THE INVENTION

This invention relates to devices and methods for treatment of bruxism and stress-related temporomandibular dysfunction. More specifically, this invention relates to an intraoral device adapted to be positioned between a person's upper and lower teeth to prevent grinding of the teeth and to reduce forces applied to the teeth, gums and jaw bones from grinding of the teeth while a person sleeps.

II. BACKGROUND AND PRIOR ART

Bruxism is the term that refers to a grinding and clenching of the teeth, unintentionally, and at inappropriate times. Bruxers (persons with bruxism) are often unaware that they have developed this habit, and often do not know that treatment is available until damage to the mouth and teeth has been done; however, each individual may experience differently bruxism symptoms which may include: abraded teeth, facial pain, oversensitive teeth, tense facial and jaw muscles, headaches, dislocation of the jaw, damage to the tooth enamel, exposing the inside of the tooth (dentin), a popping or clicking in the temporomandibular joint (TMJ), tongue indentations, and/or damage to the inside of the cheek.

While the causes of bruxism are sometimes not known or not recognized because they may resemble other conditions or medical problems, oral health specialists often point to excessive stress and certain personality types as typical causes of bruxism. Bruxism often affects persons with nervous tension such as anger, pain, or frustration, and/or persons with aggressive, hurried, or overly competitive tendencies.

Bruxism may be diagnosed during regular visits to the dentist where the teeth are examined for evidence of bruxism—often indicated by the tips of the teeth appearing flat. If symptoms are present, the condition will be observed for changes over the next several visits before a treatment program is established.

Specific treatment for bruxism will be determined by one's dentist or physician based on the person's: age, overall health, and medical history; extent of the disease; tolerance for specific medications, procedures, or therapies; expectations for the course of the disease; and/or opinion or preference.

In many cases bruxism can be successfully treated by:

a. behavior modification by teaching the patient how to rest his/her tongue, teeth, and lips properly, and learning how to rest the tongue upward may relieve discomfort on the jaw while keeping the teeth apart and lips closed, b. a specially-fitted plastic mouth appliance may be worn at night to absorb the force of biting. This appliance may help to prevent future damage to the teeth and aid in changing the patient's behavior, and c. biofeedback which involves an electronic instrument that measures the amount of muscle activity of the mouth and jaw—indicating to the patient when too much muscle activity is taking place so that the behavior can be changed. This is especially helpful for daytime bruxers. Bruxism patients may present with a variety of symptoms, including anxiety, stress, tension, depression, earache, eating disorders, insomnia, headache and/or jaw pain. Eventually, bruxing shortens and blunts the teeth being ground, and may lead to myofacial muscle pain, temporomandibular joint dysfunction and headaches. In severe, chronic cases, it can lead to arthritis of the temporomandibular joints. The jaw clenching that often accompanies bruxism can be an unconscious neuromuscular daytime activity, which should be treated as well, usually through physical therapy (recognition and stress response reduction).

Prior art bruxism management techniques include minimizing the abrasion of tooth surfaces by the wearing of an acrylic dental guard or splint, designed to the shape of an individual's upper or lower teeth from a bite mold. Mouth guards are obtained through visits to a dentist for measuring, fitting, and ongoing supervision. There are four possible goals of this treatment: constraint of the bruxing pattern such that serious damage to the temperomandibular joints is prevented, stabilization of the occlusion by minimizing the gradual changes to the positions of the teeth that typically occur with bruxism, prevention of tooth damage, and the enabling of a bruxism practitioner to judge in broad terms the extent and patterns of bruxism, through examination of the physical indentations on the surface of the splint. Dental guards typically worn on a long-term basis during every night's sleep, may be seen in U.S. Pat. Nos. 4,976,618, 5,873,365, and 6,152,138. Another type of device sometimes given to a bruxer is a repositioning splint which may look similar to a traditional night guard, but is designed to change the occlusion or "bite" of the patient.

Bruxism is associated with a person's mandible which is connected to the cranium by the temporomandibular joints located immediately in front of the ears. Rotation of the mandible about these joints is accomplished by the masticatory muscles, each of which extends from an opposite side of the mandible to a connecting point on the cranial bones. The masticatory muscles have an at rest position between their extended and contracted states. Under normal physiological conditions involving the outgrowth of a full complement of teeth, the mandibular portion of each temporomandibular joint will rest lightly in the cranial portion of the joint, and the muscles will be relaxed or at rest.

Masticatory muscle related stresses and/or pain can arise due to differences in occlusal pressures along the upper and lower dental arches. Temporomandibular joint dysfunction syndrome relates to occlusion-muscle incompatibility. Masticatory muscle accommodation is a key factor in the etiology of this syndrome. Psychological tension and stress can lead to temporomandibular joint dysfunction or bruxism in otherwise stable mouths with normal occlusion.

The most frequent jaw movement involves elevation of the mandible from its rest position into centric occlusion. Simple elevation of the mandible is normally powered almost entirely by the elevator muscles, other muscles providing only a minor bracing action. The bilateral temporals, masseters and medial pterygoids provide an excess supply of elevator motor units. Since these motor units alternate in function, with fatigued units "dropping out" to rest while others take their place, mandible elevation can be continued almost indefinitely without over fatiguing these muscles.

Occlusion-muscle dysfunction alters this condition drastically because accommodation has a highly selective effect on the masticatory muscles, increasing their activity disproportionately in certain areas of the bilateral complex. In the presence of occlusion muscle disharmony, a traumatic closure into centric occlusion requires that the mandible be adjusted every time it is elevated into occlusion. If, for example, the required adjustment is horizontal, the muscle areas capable of producing such horizontal movements must be called into activity with the same frequency as are the elevator muscle areas. Unfortunately, there are far fewer of these horizontal-adjustor motor units than elevator motor units.

Ultimately the functional capacity of these comparatively few horizontal motor units is exceeded, which triggers an exhaustion-in coordination-spasm sequence and development of the temporomandibular joint syndrome symptoms. The resulting tenderness and spasms are found most frequently in the lateral pterygoid muscles which function as anterior adjustors of mandibular placement.

In psychological stress related syndromes the muscles become fatigued as a result of nocturnal clenching or grinding of the teeth. These nocturnal activities give rise to the same symptoms as malocclusion-based temporomandibular joint dysfunction.

The sequence of muscle dysfunction spreads beyond the masticatory muscles, producing an entire constellation of primary symptoms of the temporomandibular joint pain-dysfunction syndrome. These symptoms include pain and/or tenderness in the temporomandibular joint area or masticatory muscles; "clicking" in the temporomandibular joint; limitation of jaw opening; restriction of jaw movement; and secondary symptoms which are medical in nature, being transmitted to other, more distant areas of the head and neck. These secondary symptoms probably include some of the most widespread and problematic conditions medicine has to deal with, namely, headache (including "tension" headaches), atypical facial neuralgias, tinnitus and neck and ear pain, among others. Also, certain neuromuscular disorders of the face, head and neck, shoulders, back, arms and hands can occur. These secondary symptoms are functional disturbances which exhibit no organic changes in the affected tissues, making diagnosis difficult. They are often ill-defined and difficult for the patient to describe.

These symptoms are usually diagnosed as purely medical in nature because they occur at some distance from the teeth. Their masticatory muscle origin unfortunately is not readily apparent. The usual result is that treatment is mistakenly directed to the secondary symptom's locale rather than to the underlying "invisible malocclusion." Such invisible malocclusions are common but difficult to detect. Intercuspation of the teeth appears normal, while the underlying faulty (accommodation-necessitating) craniomandibular relationship is hidden by the automatic compensatory action of the muscles. The secondary symptoms resulting from temporomandibular joint dysfunction thus are usually treated palliatively instead of having their basic cause eliminated. For malocclusion-based muscle dysfunction definitive therapy is essentially an orthopedic procedure and requires correction of the faulty cranio-mandibular relationship by a dentist. For psychological stress-related dysfunctions treatment may be addressed in other ways.

Some notable prior art methods of treating temporomandibular joint dysfunction and bruxism include clinical monitoring devices to measure the amount of pressure being asserted, splints to be worn during sleep to prevent the wearing of teeth, and behavior modification devices wherein an electrical shock is provided to the jaw muscles to interrupt a nocturnal episode without waking the patient.

The present invention provides a new intraoral device to be used when a person sleeps, this device being positioned between the person's upper and lower teeth to reduce symptoms and damage caused by bruxism and temporormandibular dysfunction. It is effective, very simple to use and relatively low in cost.

III. OBJECTS AND SUMMARY OF THE NEW INVENTION

The present invention addresses the problem of "grinding" during sleep where grinding may have the form of clenching generally axially between upper and lower teeth, or axial combined with side-to-side grinding or axial combined with front-to-rear grinding or combinations of same. This invention provides a novel intraoral device which is generally horseshoe-shaped, and in its preferred embodiment designed to have its two bite pads received between the upper and lower teeth on the left and right sides of the person's mouth. An elongated band has its opposite ends connected to the two bite pads respectively, and a central portion that extends from the bite pads as a U-shaped arch forward and around the front of the upper gums and upper teeth or around the lower gums and lower teeth.

The new device, as applied to the upper teeth, has at the top edge of the band at the front, a downward extending notch or recess to allow space for the upper frenulum, so that the band can avoid engaging and irritating the frenulum. This device can be inverted and employed with the band extending from the bite pads forward and around the lower gums and lower teeth and adjacent the lower frenulum. Whether the band is situated adjacent the upper or lower gums and teeth, the bite pads are positioned between upper and lower rear teeth and the notch at the front of the band accommodates the upper or lower frenulum respectively.

The bite pads are generally flat plates of a soft and resiliently deformable material to absorb forces applied by the upper and lower teeth to each other when grinding would occur. To achieve resilient deformability many variations of structure of the pads are possible, as described below.

The top surfaces may have upward extending projections in the form of ribs or bumps which may extend in longitudinal, parallel, transverse, diagonal, circular, random or other patterns.

Alternatively, the bottom surface of each pad may have similar projections as described above for the top surface, or top and bottom surfaces may both have such projections. Instead of ribs or bumps there may be grooves or dimples. In all these non-limiting examples, the surface allows for deformation, bending, and/or compression, so that the pad material can absorb forces applied to the teeth against each other that would otherwise cause grinding of teeth surfaces while a person sleeps.

In still additional structural forms the pads include holes or other apertures transverse of the pad surface to allow resilient flow and/or movement the plastic or rubber material forming the pad. Resilience is a requirement, since biting down and grinding will occur intermittently and repeatedly, and the device must be able to respond with sufficient strength and resilience each time forces are applied.

The device described above has the forward extending strap adapted to lie as a horseshoe shape adjacent the arch of upper teeth. As noted above, this device can be inverted for the strap to lie adjacent the arch of the lower teeth. In the former style of device there is a recess or notch extending downward to accommodate the frenulum adjacent the upper lip, and in the latter version style there is a notch extending upward to accommodate the frenulum adjacent the lower lip.

In a still further variation of the version for lower teeth with the strap lying adjacent the lower teeth, has an additional bite pad near the front and center of the strap to extend as a hook rearward over and behind the top edge of the front center teeth. This center pad then serves as an anchoring element to more securely keep the device's bite pads at the ends of the strap from moving forward or rearward during use. These bite pads are already restrained from moving rearward by the fact that the strap sits adjacent the front surface of the front teeth;

however, this latter embodiment with a front hook element will also prevent any small or large movement in the forward direction.

The bite pads described herein are energy absorbing, having a degree of resilient resistance to deformation that occurs with compression, bending and/or stretching of the material or of layers or elements of the material of the pads. As described herein, such deformation is allowed by the shape of the surface or by the composition of the pads themselves. For example, a pad may have, in section, a wave shape that rises and falls on both top and bottom surfaces or on one surface only. A still additional possibility is to have air pockets inward of the top and bottom surfaces. This would provide resilient resistance and deformation.

The new bruxism device is preferably a one-piece molded plastic article where the bite pads are relatively soft and resilient to repeatedly resist and cushion the grinding and clenching forces yet strong enough to not permit the upper and lower teeth to bite through the pads or otherwise damage or destroy them. Because of manufacture by high speed multi-cavity molds, the costs can be greatly reduced allowing the retail sale price to be so low that it is now feasible for this to be a disposable product after each one-night use. From this flow numerous advantages, including the elimination of the tasks of cleaning, disinfecting, storing and finding a reusable bruxism bite pad of the prior art, and avoid the high initial cost of such devices.

Still further advantages in use of the new device include the ease, comfort, safety and successful results. This device achieves its goals with a minimal size structure in the mouth that can become hardly noticeable as compared to far larger prior art devices. Also, this same device has the benefit of being usable upright on the lower teeth or inverted on the upper teeth, whichever is more comfortable.

A still further advantage of this new device is its essentially almost universal fit for many sizes and shapes of human mouths. The simple design, thin flexible band and relatively small bite pads allow a single device to conform easily to many different mouths. This further allows mass production at a lower cost because different many different sizes are not required, and reduces the burden on patients to find a particular size.

It is therefore an object of this invention to provide an effective and easy-to-use therapeutic apparatus for use in treating temporomandibular joint dysfunction and bruxism.

It is a further object of this invention to provide a therapeutic apparatus and method which is inexpensive to manufacture.

It is another object of this invention to provide a therapeutic apparatus which does not have to be used with direct and frequent clinical supervision.

It is also an object of this invention to provide a dental appliance which can be used "directly out-of-the-package" and will fit a great number of different persons, and thus does not have to be cut, boiled, molded or cast for each individual patient.

An additional object is to provide a bruxism protective device that is reversible and can be used with the band adjacent either to the upper or lower gums and teeth.

An exemplary first embodiment of the present invention is a one-piece molded bruxism treatment device which in upright orientation has top and bottom parts, comprising:

a. an elongated band having top and bottom edges and having a generally U-shape defining a closed front end part and legs extending rearward along a front-to-rear direction, and adapted to be positioned around the outer surfaces of a person's upper gums and teeth, said front end and legs having top and bottom edges, each of said legs terminating as a foot having a bottom edge below the bottom edges of said front end and legs, b. said front end top edge having a downward extending recess adapted to provide clearance for a person's frenulum when said device is positioned in the person's mouth with said band between said person's upper lip and upper teeth, and c. two generally planar bite pads oriented generally horizontally, each extending from one of said feet of said band medially toward the other, each of said bite pads having top and bottom surfaces and adapted to be positioned on one side of the person's jaw between the facing surfaces of a person's upper and lower teeth, and d. each said bite pads being, at least in part, resiliently deformable, thus adapted to absorb forces when said bite pad is clenched between the person's upper and lower teeth.

Another embodiment includes the additional structural feature wherein each of said pads has a medially outer edge where it extends from one of said feet and an opposite medially inner edge spaced from and generally parallel to said medially outer edge and a top surface, each of said pads further comprising a stabilizing rib along said medially inner edge and extending selectively, upward, downward or upward and downward from said top surface of said pad, each of said stabilizing ribs adapted to be situated medially inward of the inward sides of said upper and lower teeth when they clench said bite pad.

In another embodiment said band further comprises a hook element extending contiguously from said band at its closed end toward said open end and then curving upward, thus adapted to extend around the exposed edge and behind the rear surface of at least one of the user's front teeth, and thus to stabilize said device from moving forward or rearward relative to said front teeth A still further embodiment is specifically defined as being a disposable device, which is intended to be discarded after a single use.

These and other advantages of the invention will be further understood and appreciated by those skilled in the art by reference to the following written specification, claims and appended drawings.

IV. BRIEF DESCRIPTION OF THE DRAWINGS

Figure 2:
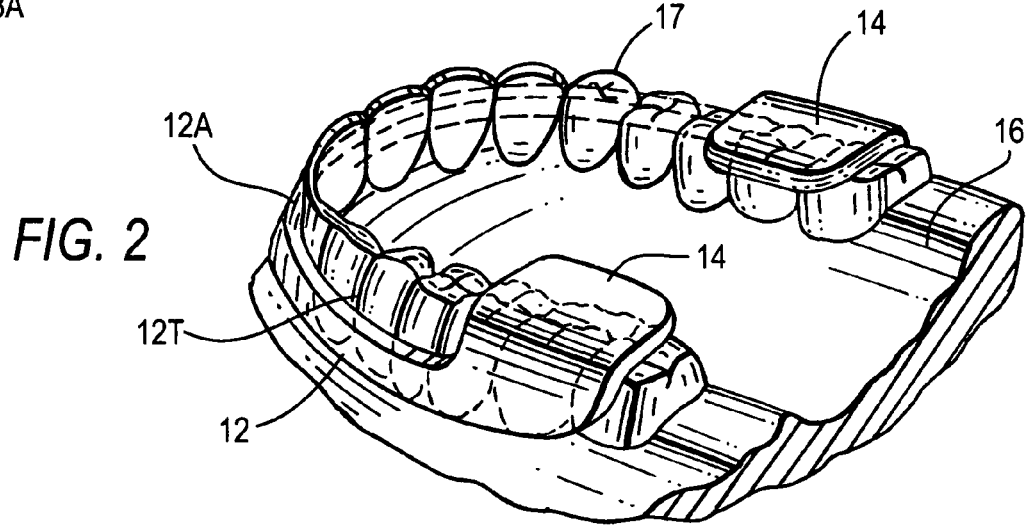
Figure 3:
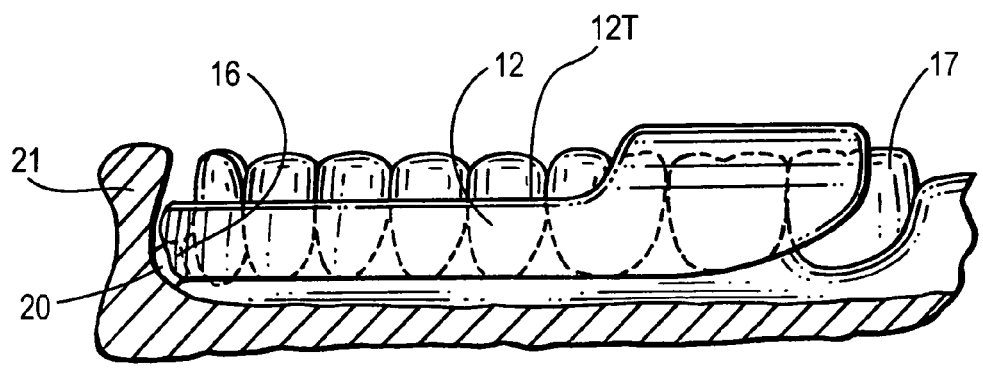
Figure 4:
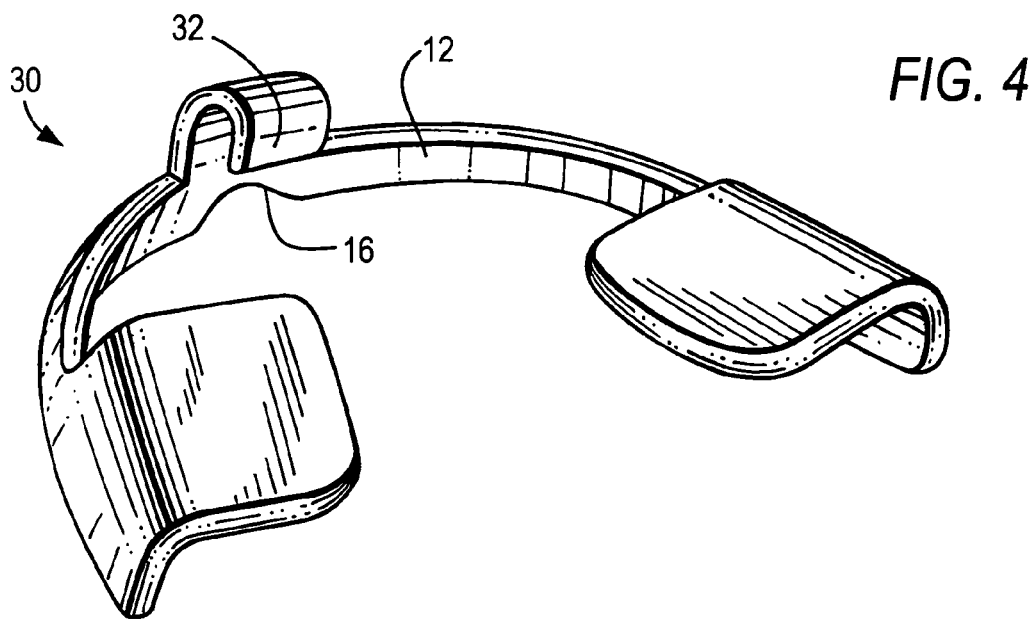
Figure 5:
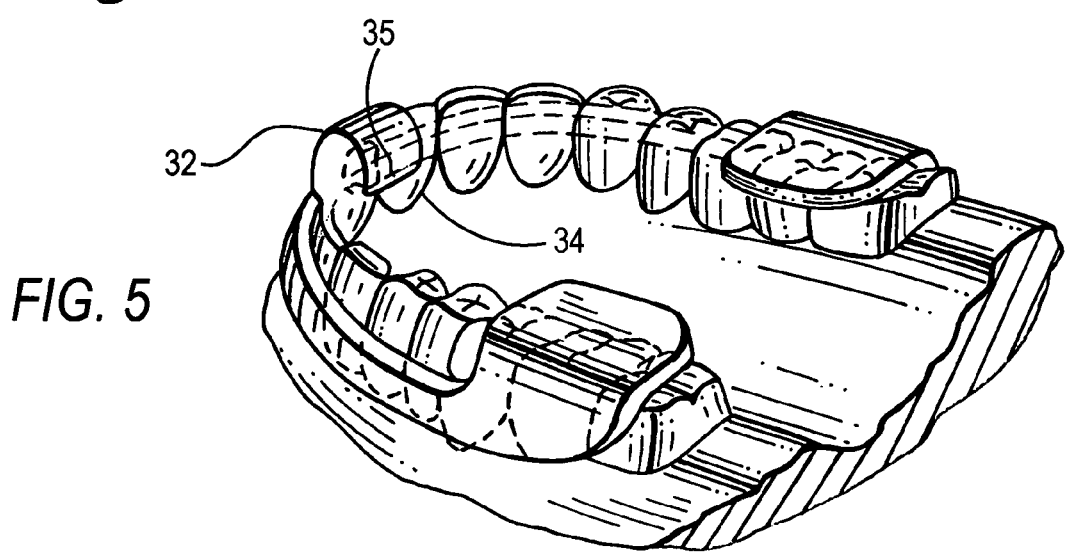
Figure 6:
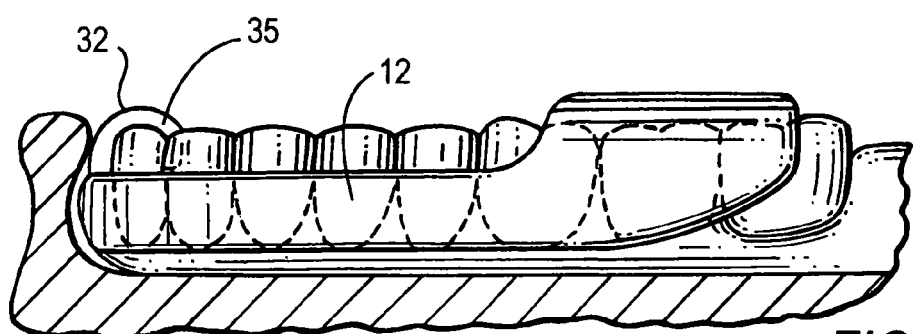

FIG. 1 is a top rear perspective view of a first embodiment of a new bruxism bite pad device for application to a lower jaw and teeth, FIG. 2 is a top left side perspective view of the bruxism bite pad of FIG. 1 as applied to a lower jaw and teeth, FIG. 3 is a left side elevation view of the bruxism bite pad of FIG. 2, FIG. 4 is a top rear perspective view of a second embodiment of the new bruxism bite pad device for application to a lower jaw and teeth but with a front hook element, FIG. 5 is a rear perspective view of the bite pad similar to the bite pad of FIG. 4 as applied to a lower jaw and teeth, FIG. 6 left side elevation view of the bite pad of FIG. 5.

Figure 17:
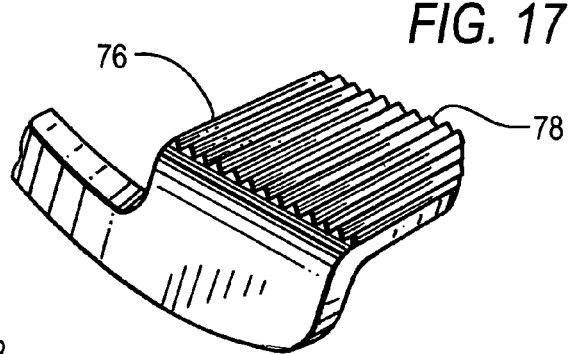
Figure 18:
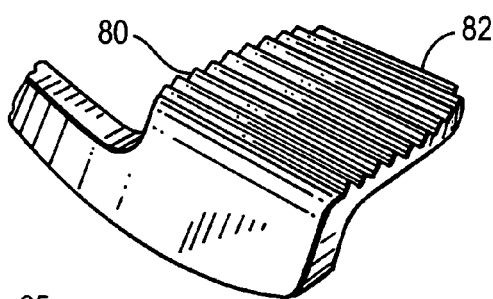
Figure 19:
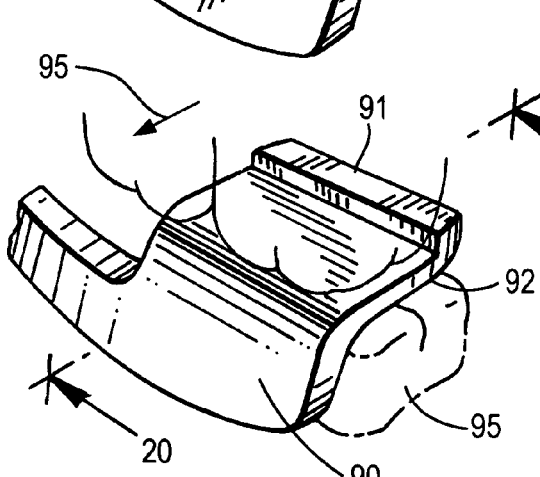
Figure 20:
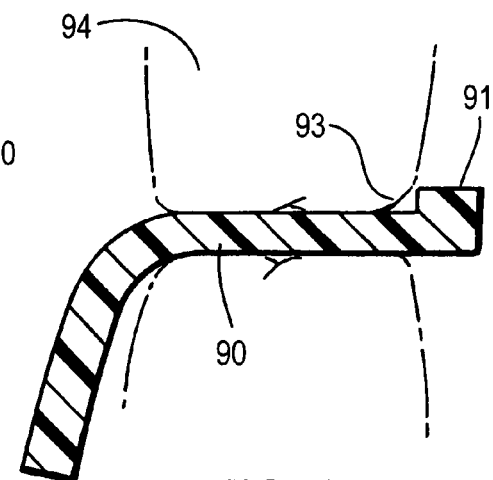
Figure 21:
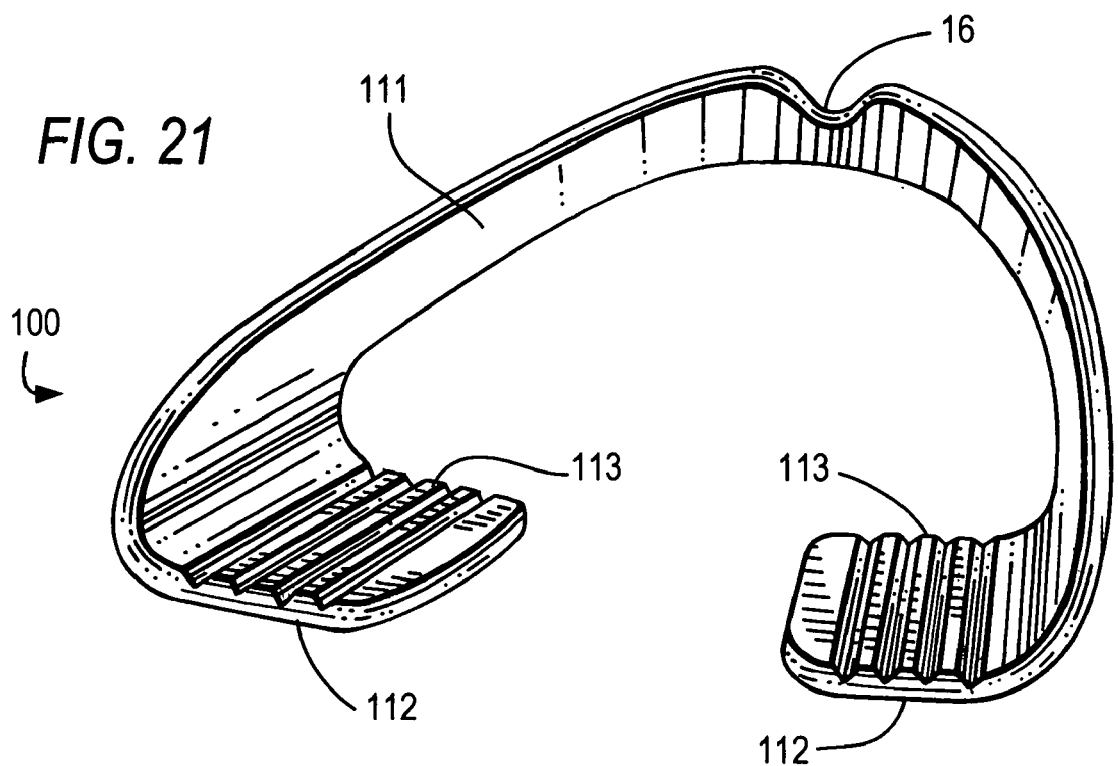
Figure 22:
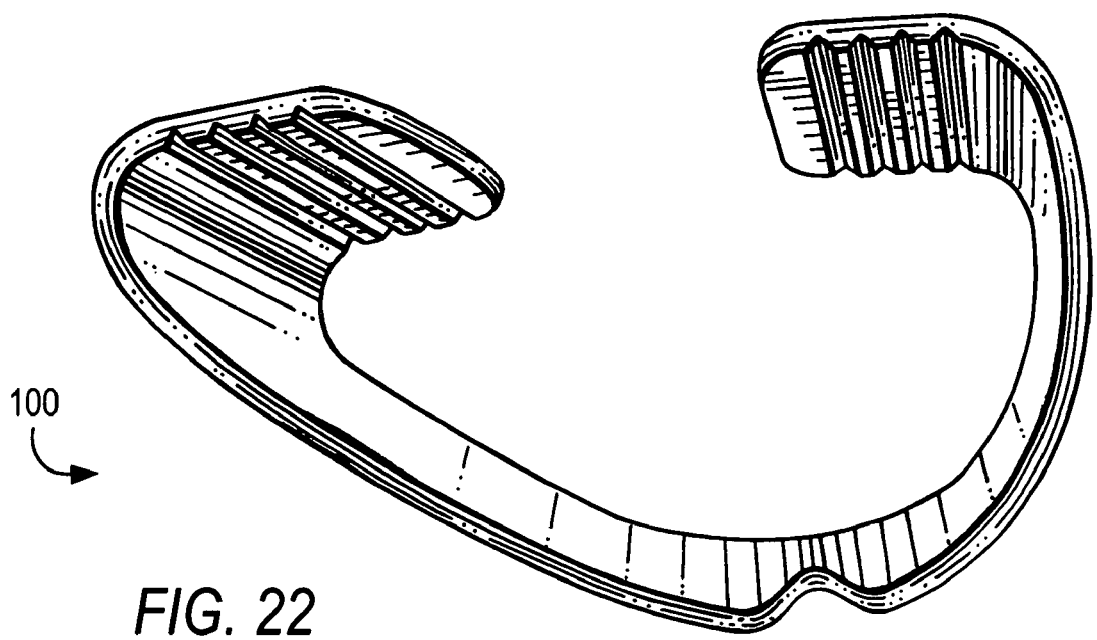

FIG. 7 is an enlarged fragmentary perspective view of a further embodiment of the hook portion of the bite pad of FIG. 4, FIGS. 8-18 are fragmentary top perspective views of eleven alternate forms of the pad portions that may be used with the bruxism devices of FIGS. 1 and 4, FIG. 19 is a top rear perspective view of a third embodiment of a bruxism bite pad device for application to a lower jaw and teeth, FIG. 20 is a sectional elevation view taken along line 20-20 in FIG. 19, FIG. 21 is a top rear perspective view of a fourth embodiment of the new bite pad for application to an upper jaw and teeth, FIG. 22 is a bottom rear perspective view thereof, FIG. 23 is a top front perspective view of a further embodiment of the new device, FIG. 24 is a top rear perspective view thereof, FIG. 25 is a bottom front perspective view thereof, and FIG. 25 is a perspective view of a further embodiment having three bite pads.

The features of the invention will become apparent from the following description of the exemplary embodiments taken in conjunction with the accompanying drawings.

V. DETAILED DESCRIPTION OF THE PREFERRED EMBODIMENTS

For convenience and clarity in describing these embodiments, similar elements or components appearing in different figures will have the same reference numbers.

FIGS. 1-3 illustrate a first embodiment of the new bruxism protective device 10 which includes an elongated band portion 12 of general U-shape having a closed end and legs 13 extending rearward along a front-to-rear direction, each of said legs terminating as a foot 13A having a top edge 13B above the top edge 13T of said front end and leg 13, and a bite pad 14 extending medially from one of said feet 13A. This is a one-piece molded device of a flexible and resilient plastic such as a thermoplastic elastomer, for example DuPont's Elvaloy™, PVC, silicones and other plastics. The required softness-toughness and resilient cushion characteristics may be achieved, for example, with material of Durometer index 00-A on the Shore scale. In a still further variation the above-mentioned material characteristics may be achieved by a laminate having a soft surface and a tougher inner layer.

Band 12 is curved to generally match the curvature of a person's jaw; however, the band is sufficiently pliable to fit exactly to different size jaws or even to lie flat in a package. At the lower edge of band 12 at the center front area is an upward extending recess 16 adapted to be positioned adjacent but without contacting or rubbing against the user's lower lip frenulum. This device may be inverted as seen in FIGS. 21-25 for use with a person's upper jaw, with recess 16 then adjacent the user's upper frenulum.

FIGS. 2 and 3 illustrate the device 10 of FIG. 1 as applied to a person's lower jaw 16 and teeth 17. As seen, the front portion 12A band 12 is situated around the front area of the gums and teeth, and the remainder of the band extends around and adjacent the sides of the jaw, until bite pads 14 are placed on top of lower teeth 17 on the left and right sides respectively. When the plane of band 12 is generally vertical bite pads 14 are in a generally horizontal plane at an elevation above the top edge 12T of the band, so they can extend from the outside and then over the top surfaces of teeth 17. As represented schematically in FIG. 3, recess 16 at the front of band 12 fits over and above and without interfering with the lower lip frenulum 20 which is situated between the lower lip 21 and the lower gum.

FIGS. 4-6 illustrate a second embodiment 30 of the new bruxism protective device which differs from the first embodiment 10 in FIGS. 1-3 by the addition of a hook element 32 at the top front area of band 12 and directly above the recess 16. As shown in FIGS. 5 and 6, hook element 32, is situated to lie over the top of the lower front teeth 34 and have its rear tab portion 35 extend downward behind said front teeth.

Bruxism device 30 is used generally the same as device 10 in FIGS. 1-3, except that with a hook element 32, device 30 is precluded from sliding forward, which might occur when the upper and lower jaws and teeth are separated and no pressure is applied to bite pads 14. Hook element 32 is an added stabilization feature, which is not required in the simpler design of device 10. Hook element 32 can furthermore serve as an auxiliary bite pad between upper and lower front teeth.

FIG. 7 illustrates a variation 36 of the above-mentioned hook element, this variation extending rearward and downward as tab 37 with laterally extending left and right ears 38 and 39 for enhanced engagement and stability with the lower front teeth.

FIGS. 8-18 illustrate a variety of alternate forms of bite pads which will be described in detail as follows. In FIG. 8 bite pad 40 has a wavy or waffle construction of laterally extending ribs 41 forming hills 42 and valleys 43. FIG. 9 shows bite pad 44 which is essentially flat along the top and bottom surfaces, generally as appears in FIGS. 1 and 4.

Figure 14:
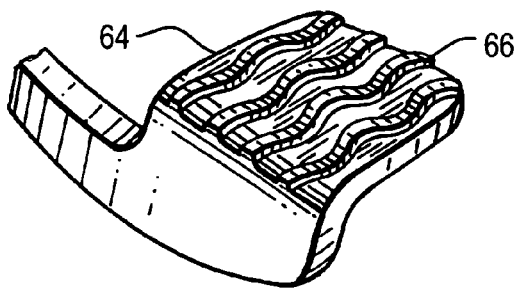
Figure 15:
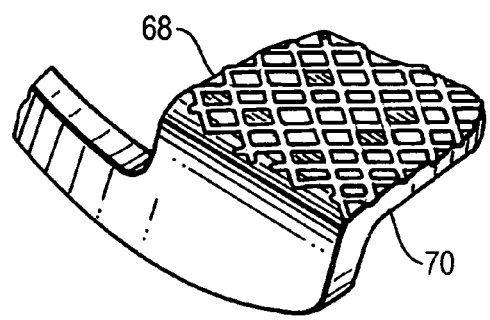
Figure 16:
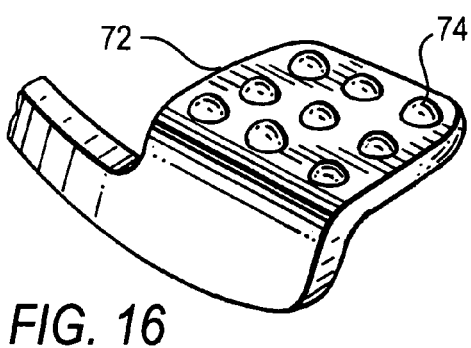

FIG. 10 shows a bite pad 48 which has a plurality of round holes 49 extending vertically through the pad between its top and bottom surfaces. FIG. 11 shows bite pad 50 with longitudinally extending ribs 51 defining hills 52 and valleys 53, these wavy ribs extending longitudinally as compared with ribs 41 in FIG. 8 which extend laterally or transversely. In FIG. 12 bite pad 54 has diagonally intersecting grooves 56 which extend downward into the top surface of the bite pad. In FIG. 13 the bite pad 60 has parallel grooves 62 extending diagonally. In FIG. 14 bite pad 64 has wavy grooves 66 extending laterally. In FIG. 15 bite pad 68 has diagonal ribs 70 which extend upward from the top surface of the bite pad. In FIG. 16 bite pad 72 has upward extending generally around or oval bumps 74. In FIG. 17 bite pad 76 has closely spaced small ribs 78 extending transversely. In FIG. 18 bite pad 80 has a plurality of closely spaced small ribs 82 extending longitudinally.

FIGS. 19 and 20 illustrate a still further embodiment of the bite pad 90, which has an upward extending longitudinal stabilizing rib 91 at the inward or medial edge 92 of bite pad 90. FIG. 20 shows also in dashed line an optional alternative downward extending stabilizing rib 91A, and a further alternative would be to include both upward and downward stabilizing ribs 91 and 91A. As seen in FIGS. 19 and 20, in use of bite pad 90, its stabilizing rib 91 is situated slightly inward of the lower inward edge 93 of the upper tooth 94. So long as the upper tooth 94 and immediately adjacent lower tooth 95 are closed down on bite pad 90, stabilizing rib 91 will prevent bite pad 90 from sliding laterally in the direction of the arrow 95 and outward from between said upper and lower teeth.

In regard to all of the bite pads, the objective is to have a compressible material which can resist compressive forces between upper and lower teeth in a cushioning manner with a predetermined amount of resistance and return to its normal state after compression. Compression is allowed because of the characteristics of the plastic or rubber material from which the bite pad is made, and/or from the geometry or engineered structure that has been illustrated in the numerous embodiments of FIGS. 7-17. Deflection and/or deformation can occur not only from inherent compressibility of the bite pad material, but also when ribs are pushed into adjacent grooves, or when hills are pressed into adjacent valleys, or bumps are squashed down, or projections are bent, or any bite pad material is deformed and pushed into adjacent depressions or apertures, providing relief space for resilient plastic flow of the bite pad material.

Thus, bite pads can resiliently deflect, compress, bend or otherwise deform by compressing or flattening of "hills" of the bite pad of FIGS. 8 and 11, by flowing of bite pad material into aperture areas in pads of FIG. 10, by bending, compressing or flowing rib material into adjacent groove areas in pads of FIGS. 11-15 and 17-18, or by compressing projections in pads of FIG. 16.

FIGS. 21 and 22 illustrate a still further embodiment 100 of the new bruxism protective device, this embodiment being essentially the same as device 10 in FIG. 1, but inverted and used with band 111 adjacent to the upper teeth and upper jaw, and bite pads 112 still situated between sets of upper and lower rear teeth. With device 100, its recess 16 extends upward instead of downward to be clear of the upper frenulum. In this particular device 100, bite pads 112 have in their upper surfaces longitudinal spaced apart grooves 113.

FIGS. 23-25 show a still further embodiment 115 with a modified front bite plate-hook part 116 and modified bite plates 118, the entire structure having more smooth transition areas between component parts which is beneficial for manufacture, appearance and ultimate use. In this embodiment, as with the embodiments of FIGS. 1, 4 and 21, the bite pads are a continuous extension of the band at an elevation and in a plane above the top edge of the band.

FIG. 26 shows a still further embodiment 120 of the new bruxism protective device having left and right bite pads 121, 122 and front bite pad 123. In this embodiment all three bite pads are at the same elevation; however, the elevation and width of the front bite pad may vary. As seen each of the FIGS. 1-6 embodiments is molded as a one-piece device with bite pads extending from the and with a continuous unbroken surface.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

The invention claimed is:

1. A one-piece molded bruxism treatment device which in upright orientation has top and bottom parts, comprising:
   a. an elongated flexible band having top and bottom edges and having a generally U-shape defining a closed front end part and legs extending rearward along a front-to-rear direction, and adapted to be positioned around the outer surfaces of a person's upper gums and teeth, said front end and legs having top and bottom edges, each of said legs terminating as a foot having a bottom edge below the bottom edges of said front end and legs,
   b. said front end top edge having a downward extending recess adapted to provide clearance for a person's frenulum when said device is positioned in the person's mouth with said band between said person's upper lip and upper teeth, and
   c. two generally planar bite pads oriented generally horizontally, each molded with said band to extend contiguously from one of said feet of said band medially toward the other, each of said bite pads having top and bottom surfaces and adapted to be positioned on one side of the person's jaw between the facing surfaces of a person's upper and lower teeth, and
   d. each said bite pads being, resiliently deformable, thus adapted to absorb forces when said bite pad is clenched between the person's upper and lower teeth.

2. The bruxism treatment device according to claim 1, wherein said bite pads extend in a generally common plane from said opposite feet respectively of said band at said elevation below the bottom edges of said front end and legs.

3. The bruxism treatment device according to claim 1 wherein each of said pads is resiliently compressible when clinched between the person's upper and lower teeth.

4. The bruxism treatment device according to claim 1 wherein each of said pads has length in said front-to-rear direction of said band of about 15-30 mm and width of about 8-12 mm in a direction generally perpendicular to said front-to-rear direction.

5. The bruxism treatment device according to claim 1 formed of plastic having compressibility defined by a Shore A hardness 78/27.

6. The bruxism device according to claim 1 formed of plastic that can resist a compressive force of about 200 psi.

7. The bruxism protective device according to claim 1 wherein said band has thickness of about 2 mm and said bite pads have thickness of about 2 mm.

8. A one-piece molded bruxism treatment device which in upright orientation has top and bottom parts, comprising:
   a. an elongated flexible band having top and bottom edges and having a generally U-shape defining a closed front end part and legs extending rearward along a front-to-rear direction, and adapted to be positioned around the outer surfaces of a person's upper gums and teeth, said front end and legs having top and bottom edges, each of said legs terminating as a foot,
   b. said front end top edge having a downward extending recess adapted to provide clearance for a person's frenulum when said device is positioned in the person's mouth with said band between said person's upper lip and upper teeth, and
   c. two generally planar bite pads oriented generally horizontally, each molded with said band to extend contiguously from one of said feet of said band medially toward the other, each of said bite pads having top and bottom surfaces and adapted to be positioned on one side of the person's jaw between the facing surfaces of a person's upper and lower teeth, and
   d. each said bite pads being resiliently deformable when said bite pad is clenched between the person's upper and lower teeth.

9. A bruxism treatment device formed as a molded one-piece device which in upright orientation has top and bottom parts, comprising:
   a. an elongated flexible band having a generally U-shape defining a closed front end part and legs extending rearward with bite pads molded with said band to extend continuously from ends of said legs of said band, and adapted to be positioned around the outer surfaces of a person's upper gums and teeth, said front end and legs having top and bottom edges, each of said legs terminating as a foot that extends lower than said bottom edges of said front end part and legs,
   b. said front end part top edge having a downward extending recess adapted to provide clearance for a person's frenulum when said device is positioned in the person's mouth with said band between said person's upper lip and upper teeth, and
   c. said bite pads being generally planar and oriented generally horizontally, each molded with said band to extend contiguously from one of said feet medially toward the other of said feet, each of said bite pads having top and bottom surfaces and adapted to be positioned between the facing surfaces of a person's upper and lower teeth on one side of the person's jaw, and d. each said bite pads being resiliently deformable, thus adapted to absorb forces when said bite pad is clenched between the person's upper and lower teeth.

* * * * *

UNITED STATES PATENT AND TRADEMARK OFFICE
CERTIFICATE OF CORRECTION

PATENT NO.        : 8,196,587 B2                                        Page 1 of 1
APPLICATION NO.   : 12/316922
DATED             : June 12, 2012
INVENTOR(S)       : Ingram S. Chodorow It is certified that error appears in the above-identified patent and that said Letters Patent is hereby corrected as shown below:

Column 9, line 35, "pads extending from the and with a continuous unbroken" should read -- pads extending from the band with a continuous unbroken --

Signed and Sealed this
Thirtieth Day of October, 2012

David J. Kappos
*Director of the United States Patent and Trademark Office*